(12) United States Patent
Hammen et al.

(10) Patent No.: US 11,771,832 B2
(45) Date of Patent: Oct. 3, 2023

(54) CONSERVING POWER IN AN INJECTION DEVICE

(71) Applicant: SANOFI, Paris (FR)

(72) Inventors: Dietmar Hammen, Frankfurt am Main (DE); Thomas Klemm, Frankfurt am Main (DE)

(73) Assignee: Sanofi, Paris (FR)

( * ) Notice: Subject to any disclaimer, the term of this patent is extended or adjusted under 35 U.S.C. 154(b) by 421 days.

(21) Appl. No.: 16/763,380

(22) PCT Filed: Nov. 12, 2018

(86) PCT No.: PCT/EP2018/080901
§ 371 (c)(1),
(2) Date: May 12, 2020

(87) PCT Pub. No.: WO2019/096726
PCT Pub. Date: May 23, 2019

(65) Prior Publication Data
US 2021/0069421 A1  Mar. 11, 2021

(30) Foreign Application Priority Data
Nov. 14, 2017 (EP) ..................... 17306573

(51) Int. Cl.
*A61M 5/315* (2006.01)
*A61M 5/00* (2006.01)
(Continued)

(52) U.S. Cl.
CPC ........ *A61M 5/31511* (2013.01); *A61M 5/002* (2013.01); *A61M 5/28* (2013.01);
(Continued)

(58) Field of Classification Search
CPC ................ A61M 5/31511; A61M 5/28; A61M 2205/0272; A61M 2205/3317; A61M 2205/8212
See application file for complete search history.

(56) References Cited

U.S. PATENT DOCUMENTS

| | | | |
|---|---|---|---|
| 2011/0009821 | A1 | 1/2011 | Jespersen et al. |
| 2012/0203178 | A1 | 8/2012 | Tverskoy |

(Continued)

FOREIGN PATENT DOCUMENTS

| | | |
|---|---|---|
| JP | 2012-519028 | 8/2012 |
| JP | 2017-520298 | 7/2017 |

(Continued)

OTHER PUBLICATIONS

Levido, Andrew; Ferroelectric RAM Oct. 28, 2020 https://circuitcellar.com/resources/ferroelectric-ram/ (Year: 2020).*

(Continued)

*Primary Examiner* — Bradley J Osinski
(74) *Attorney, Agent, or Firm* — Fish & Richardson P.C.

(57) ABSTRACT

A drug injection device comprising: a cartridge configured to hold a volume of a drug; one or more processors configured to operate in at least an enabled state and a sleep state, wherein the one or more processors are configured to control an operation of the drug injection device while the one or more processors are in the enabled state; a member disposed in the cartridge, the member including at least two conductive surfaces electrically connected to the one or more processors; and a drive mechanism including a conductive element spaced from the at least two conductive surfaces, wherein the one or more processors are configured to enter the enabled state from the sleep state when the conductive element makes electrical contact with the at least two conductive surfaces.

7 Claims, 11 Drawing Sheets

(51) Int. Cl.
*A61M 5/28* (2006.01)
*A61M 5/14* (2006.01)

(52) U.S. Cl.
CPC ... *A61M 5/3155* (2013.01); *A61M 2005/1402* (2013.01); *A61M 2205/0272* (2013.01); *A61M 2205/3306* (2013.01); *A61M 2205/3317* (2013.01); *A61M 2205/3368* (2013.01); *A61M 2205/3584* (2013.01); *A61M 2205/36* (2013.01); *A61M 2205/50* (2013.01); *A61M 2205/581* (2013.01); *A61M 2205/8212* (2013.01)

(56) References Cited

U.S. PATENT DOCUMENTS

| | | | |
|---|---|---|---|
| 2012/0268741 | A1 | 10/2012 | Pommereau et al. |
| 2015/0202376 | A1* | 7/2015 | Haupt ............... A61M 5/31525 604/189 |
| 2015/0320934 | A1 | 11/2015 | Draper et al. |
| 2016/0259913 | A1* | 9/2016 | Yu ..................... A61M 5/31511 |
| 2017/0281877 | A1 | 10/2017 | Marlin et al. |
| 2017/0312430 | A1 | 11/2017 | Schleicher et al. |
| 2017/0312455 | A1 | 11/2017 | Mirov et al. |

FOREIGN PATENT DOCUMENTS

| | | |
|---|---|---|
| JP | 2017-524399 | 8/2017 |
| WO | WO 2010/098927 | 9/2010 |
| WO | WO 2010/098931 | 9/2010 |
| WO | WO 2015/187793 | 12/2015 |
| WO | WO 2017/050781 | 3/2017 |
| WO | WO 2017/155672 | 9/2017 |

OTHER PUBLICATIONS

PCT International Preliminary Report on Patentability in Application No. PCT/EP2018/080901, dated May 19, 2020, 12 pages.
PCT International Search Report and Written Opinion in Application No. PCT/EP2018/080901, dated Jun. 4, 2019, 18 pages.

* cited by examiner

CONSERVING POWER IN AN INJECTION DEVICE

CROSS REFERENCE TO RELATED APPLICATIONS

The present application is the national stage entry of International Patent Application No. PCT/EP2018/080901, filed on Nov. 12, 2018, and claims priority to Application No. EP 17306573.1, filed on Nov. 14, 2017, the entire disclosures of which are incorporated herein by reference.

This disclosure relates to conserving power, and more particularly, to conserving power in an injection device.

A variety of diseases exist that require treatment by injection of a medicament. Such injection can be performed using injection devices, which are applied either by medical personnel or by patients themselves. As an example, type-1 and type-2 diabetes can be treated by patients themselves by injection of insulin doses, for example once or several times per day. For instance, a pre-filled disposable insulin pen or autoinjector can be used as an injection device. Alternatively, a re-usable pen or autoinjector may be used. A re-usable pen or autoinjector allows replacement of an empty medicament cartridge by a new one. Either type of pen or autoinjector may come with a set of one-way needles that are replaced before each use.

Described herein are systems and techniques for preserving power in an injection device. To ensure that the injection device is capable of full functionality for use by a patient, it may be beneficial to preserve as much power as possible when the injection device is not in use. For example, during and after manufacture of the injection device but before use by the patient, there may exist instances in which the injection device should be powered on (e.g., during test of electronics of the injection device). However, even when the injection device is powered off, there may exist instances in which power is depleted from the power source (e.g., due to standby power loss). To prevent such loss of power, the microcontroller may be configured to operate in a sleep state (e.g., a deep sleep state). In such a sleep state, the microcontroller may drastically reduce and/or eliminate standby power loss in the battery. For example, the microcontroller may draw significantly less than ten nanoamps while operating in the sleep state. In some embodiments, the injection device may be capable of achieving a lifetime of approximately 4-5 years by utilizing the sleep state of the microcontroller and/or by electrically isolating the microcontroller from the battery when not in use.

In some embodiments, a drug injection device includes a cartridge configured to hold a volume of a drug, and one or more processors configured to operate in at least an enabled state and a sleep state. The one or more processors are configured to control an operation of the drug injection device while the one or more processors are in the enabled state. The drug injection device also includes a member in the cartridge. The member includes at least two conductive surfaces electrically connected to the one or more processors. The drug injection device also includes a drive mechanism that includes a conductive element spaced from the at least two conductive surfaces. The one or more processors are configured to enter the enabled state from the sleep state when the conductive element makes electrical contact with the at least two conductive surfaces. In some embodiments, the member is a stopper, and the conductive element is disposed on a bottom surface of a plunger of the drive mechanism.

In some embodiments, the conductive element is configured to move toward the member and make electrical contact with the at least two conductive surfaces in response to engagement of the drive mechanism. The drive mechanism may be engaged during priming of the drug injection device. The conductive element making electrical contact with the at least two conductive surfaces may cause a reset circuit in the one or more processors to be activated.

In some embodiments, the drug injection device also includes one or more non-transitory computer-readable medium storing instructions operable to cause the one or more processors to control the operation of the drug injection device. The one or more non-transitory computer-readable medium may include a ferroelectric random access memory (FRAM) that is configured to store data without a continuous supply of power.

In some embodiments, a drug injection device includes a cartridge configured to hold a volume of a drug, and one or more processors configured to operate in at least an enabled state and a sleep state. The one or more processors are configured to control an operation of the drug injection device while the one or more processors are in the enabled state. The drug injection device also includes a sensor in communication with the one or more processors. The sensor is configured to cause the one or more processors to enter the enabled state from the sleep state in response to a stimulus. In some embodiments, the sensor is a magnetoresistance sensor that is configured to cause the one or more processors to enter the enabled state when the magnetoresistance sensor ceases to sense a magnetic field that satisfies a threshold magnitude. The drug injection device may be configured to reside in packaging that includes a magnet that provides the magnetic field that satisfies the threshold magnitude, and the one or more processors may enter the enabled state when the drug injection device is removed from the packaging. In some embodiments, the drug injection device also includes a cover that is configured to attach to a housing of the drug injection device. The cover may include a magnet that provides the magnetic field that satisfies the threshold magnitude, and the one or more processors may enter the enabled state when the cover is removed from the housing.

In some embodiments, the sensor includes one or both of a photodiode or a photoresistor that is configured to cause the one or more processors to enter the enabled state when the photodiode or photoresistor senses light that satisfies a threshold intensity. In some embodiments, the sensor is a thermistor that is configured to cause the one or more processors to enter the enabled state when the thermistor senses a temperature that satisfies a threshold. In some embodiments, the sensor is an X-Ray diode that is configured to cause the one or more processors to enter the enabled state when the X-Ray diode senses X-Ray radiation.

In some embodiments, the sensor is a Wi-Fi sensor that is configured to cause the one or more processors to enter the enabled state when the Wi-Fi sensor senses Wi-Fi radiation. The drug injection device may be configured to reside in packaging that shields Wi-Fi radiation, and the one or more processors may enter the enabled state when the drug injection device is removed from the packaging.

In some embodiments, the sensor is a Near Field Communication (NFC) sensor that is configured to cause the one or more processors to enter the enabled state when the NFC sensor receives an NFC signal from a computing device. The computing device may be a mobile phone. In some embodiments, the sensor includes a resonant circuit that is configured to cause the one or more processors to enter the enabled state when the resonant circuit senses a magnetic field having a resonant frequency.

In some embodiments, a system includes a drug injection device that includes a cartridge configured to hold a volume of a drug, and one or more processors configured to operate in at least an enabled state and a sleep state. The one or more processors are configured to control an operation of the drug injection device while the one or more processors are in the enabled state. The drug injection device also includes a Wi-Fi sensor in communication with the one or more processors. The Wi-Fi sensor is configured to cause the one or more processors to enter the enabled state from the sleep state when the Wi-Fi sensor senses Wi-Fi radiation. The system also includes packaging configured to contain the drug injection device after manufacture and until initial use by a patient. The packaging includes a material that shields Wi-Fi radiation to prevent the one or more processor from entering the enabled state until the drug injection device is removed from the packaging.

In some embodiments, a drug injection device includes a cartridge configured to hold a volume of a drug, and one or more processors configured to operate in at least an enabled state and a sleep state. The one or more processors are configured to control an operation of the drug injection device while the one or more processors are in the enabled state. The drug injection device also includes a circuit electrically connected to the one or more processors. The circuit includes one or more transistors and one or more fuses. The one or more transistors are configured to cause the one or more processors to enter the enabled state from the sleep state in response to the one or more fuses being blown. The one or more fuses may be blown in response to application of laser light, which may be applied by an electronic device provided with the drug injection device. Heat provided by the laser light may cause the one or more fuses to blow.

In some embodiments, a drug injection device includes a cartridge configured to hold a volume of a drug, and one or more processors configured to control an operation of the drug injection device. The drug injection device also includes a circuit electrically connected to the one or more processors. The circuit includes a battery, one or more transistors, and one or more fuses. The one or more transistors electrically isolate the one or more processors from the battery when the one or more fuses are in a non-blown state, and the one or more transistors electrically connect the one or more processors to the battery when the one or more fuses are blown. The one or more fuses may be blown in response to application of laser light, which may be applied by an electronic device provided with the drug injection device. Heat provided by the laser light may cause the one or more fuses to blow.

In some embodiments, a drug injection device includes a cartridge configured to hold a volume of a drug, one or more processors configured to control an operation of the drug injection device, and a cover configured to attach to a housing of the drug injection device. The cover includes a first inductive coil configured to electrically connect to a power source. The drug injection device also includes a circuit electrically connected to the one or more processors. The circuit includes a second inductive coil and a supercapacitor. The second inductive coil is configured to receive an electromagnetic field from the first inductive coil and generate power to be stored by the supercapacitor and provided to the one or more processors.

Like reference symbols in the various drawings indicate like elements.

Figure 1:
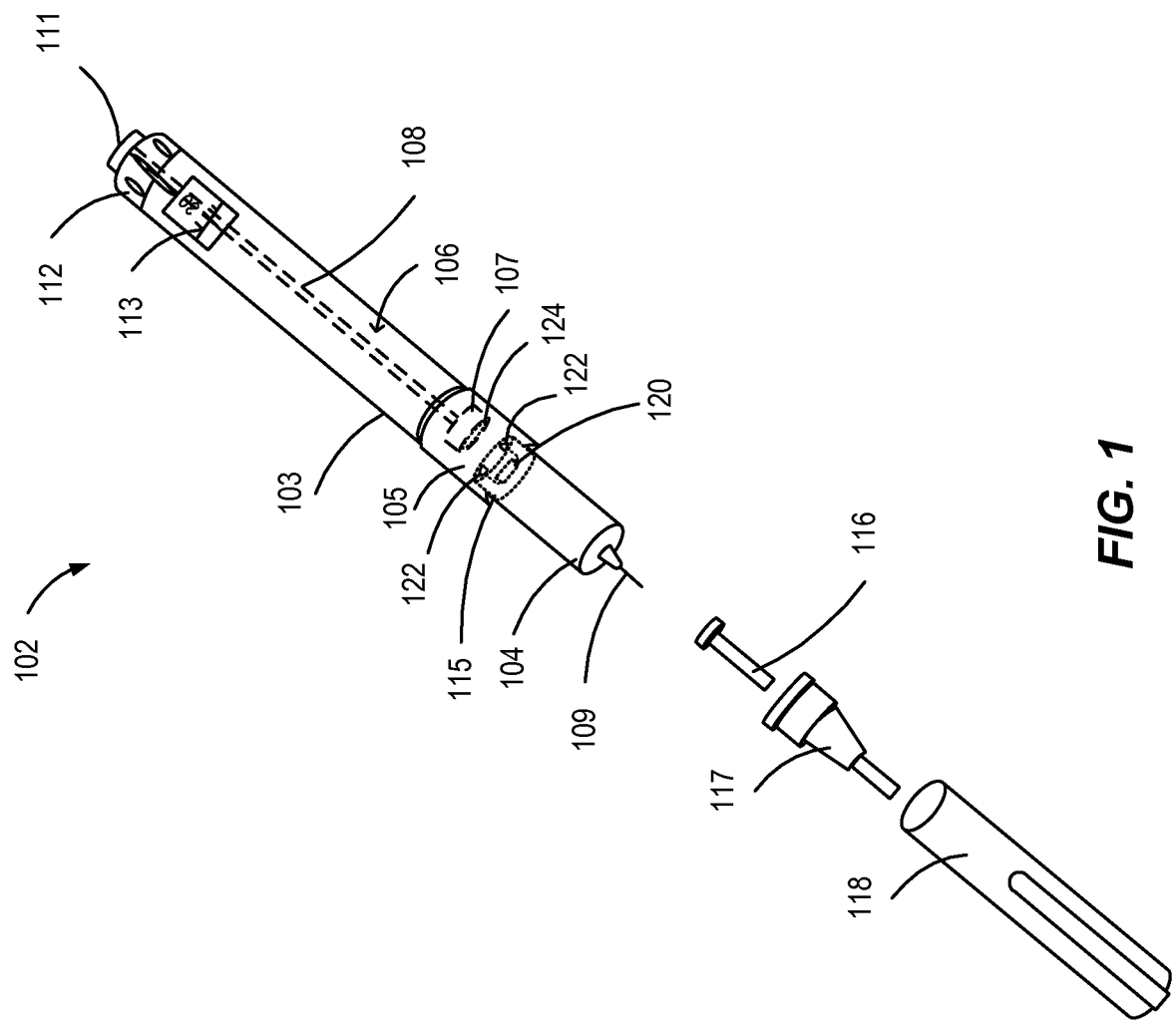
FIGS. 1-9 show various examples of injection devices.

The subject matter described herein will largely be described with reference to a drug delivery device such as an injection device (e.g., an insulin injection device). However, the systems and techniques described herein are not limited to such applications, and may equally well be deployed with injection devices that eject other medicaments, or with other types of medical devices (e.g., pumps).

The term "drug delivery device" shall encompass any type of device or system configured to dispense a volume of a drug into a human or animal body. The volume can typically range from about 1 µl to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, which can, in certain embodiments, be a small gauge needle (e.g., greater than about 24 gauge, and including 27, 29, or 31 gauge). In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures. In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

FIG. 1 shows an example of an injection device 102. The injection device 102 may be a pre-filled, disposable or reusable injection pen. The injection device 102 includes a housing 103 and a cartridge 104. The cartridge 104 is configured to hold a volume of medicament (e.g., in fluid form). In some embodiments, the cartridge 104 is a medicament container, such as an insulin container. At least a portion of the cartridge 104 resides within the housing 103 of the injection device 102 and/or a cartridge housing 105, and therefore some or all of the cartridge 104 may not be readily visible.

The injection device 102 includes a drive mechanism 106 that is configured to cause the medicament to be ejected from the cartridge 104. The drive mechanism 106 includes a plunger 107 that is movably disposed in the cartridge 104 and a piston 108 (e.g., a plunger arm). A member 115 (e.g., a stopper) is also disposed in the cartridge 104 proximate to the plunger 107. In an initial state (e.g., before an injection), the member 115 is spaced from the plunger 107 by a relatively short distance (e.g., less than 1 mm). The piston 108 is configured to cause the plunger 107 to move from a proximal end of the cartridge 104 toward the member 115. In particular, when the drive mechanism 106 is engaged, the piston 108 drives the plunger 107 toward the member 115 such that the plunger 107 and the member 115 make physical contact with each other. The piston 108 then continues to traverse the cartridge 104, thereby causing the plunger 107 and the member 115 to displace and dispense fluid through a needle 109 disposed at a distal end of the cartridge 104. The needle 109 includes an aperture through which the fluid is dispensed. In some embodiments, the needle 109 and/or the cartridge 104 are threaded such that the needle 109 can be screwed onto the cartridge 104 for attachment. The needle 109 can be protected by an inner needle cap 116 and an outer needle cap 117, which in turn can be covered by a cover 118.

A medicament dose (e.g., such as an insulin dose) to be ejected from injection device 102 can be selected by turning a dosage knob 112, and the selected dose can be displayed by a dosage window 113. In some examples, the dosage window 113 is a display, such as an electronic display. In some examples, the selected dose can be displayed in multiples of International Units (IU), wherein one IU is the biological equivalent of about 45.5 micrograms of medicament such as pure crystalline insulin (e.g., 1/22 mg). An example of a selected dose displayed in the dosage window 113 may, for example, be 30 IUs, as shown in FIG. 1. In some examples, the selected dose may be displayed differently, for example, by a non-electronic display. In some examples, the dosage window 113 relates to the section of the injection device 102 through or on which the selected dosage is visible.

Turning the dosage knob 112 may cause a mechanical click sound to provide acoustical feedback to a user. The numbers displayed in the dosage window 113 are printed on a sleeve that is contained in the housing 103 and mechanically interacts with the drive mechanism 106. When the needle 109 is inserted into a skin portion of the patient, and then an injection button 111 is pressed, the medicament is ejected from the injection device 102. Ejection of the dose may also cause a mechanical click sound. Such a mechanical click sound may be different from the sounds produced when the dosage knob 112 is turned. The injection device 102 may be used for several injection processes until either the cartridge 104 is empty or the expiration date of the injection device 102 (e.g., 28 days after the first use) is reached.

In some examples, before using the injection device 102 for the first time, it may be necessary to perform a "prime shot" to remove air from the cartridge 104 and the needle 109, for example, by selecting two units of medicament and pressing the injection button 111 while holding the injection device 102 with the needle 109 oriented upwards.

The injection device 102 includes a microcontroller 120 that may include one or more processors and one or more memory devices. In some embodiments, the one or more memory devices include one or more non-transitory computer-readable medium storing instructions operable to cause the one or more processors to perform operations (e.g., control an operation of the injection device 102). In some embodiments, the one or more non-transitory computer readable medium may include a ferroelectric random access memory (FRAM) that is configured to store data without a continuous supply of power. Such FRAM may be used to further reduce power consumption in the injection device 102 when not in use. Operations that can be performed by the one or more processors may include determining an amount (e.g., dosage) of a medicament administered by the injection device 102, recording and/or transmitting information related to an administered dosage, controlling an electronic display of the injection device 102, etc. As illustrated in FIG. 1, in some embodiments, the microcontroller 120 is incorporated into the member 115. The injection device may also include a power source such as a battery, for example, a coin cell battery, for powering the microcontroller 120. The battery may also be incorporated into the member 115 proximate to the microcontroller 120.

To ensure that the injection device 102 is capable of full functionality for use by a patient, it may be beneficial to preserve as much power as possible when the injection device 102 is not in use. For example, after manufacture of the injection device 102 but before use by the patient, there may exist instances in which the injection device 102 should be powered on. However, even when the injection device 102 is powered off, there may exist instances in which power is depleted from the power source (e.g., due to "vampire draw" or standby power loss). To prevent such loss of power, the microcontroller 120 may be configured to operate in a sleep state (e.g., a deep sleep state). In such a sleep state, the microcontroller 120 may drastically reduce and/or eliminate standby power loss in the battery. For example, the microcontroller 120 may draw significantly less than ten nanoamps while operating in the sleep state. In some embodiments, the injection device 102 may be capable of achieving a lifetime of approximately 4-5 years by utilizing the sleep state of the microcontroller 120 and/or by electrically isolating the microcontroller 120 from the battery when not in use.

The microcontroller 120 may enter the sleep state in response to a command. The command may include a simple signal received by the microcontroller 120 indicating that the sleep state is to be initiated. In some embodiments, the command may include application of an input voltage or current on one or more pins of the microcontroller 120. When operating in the sleep state, functionality of the microcontroller 120 may be limited. For example, the microcontroller 120 may be unable to control one or more operations of the injection device 102 during sleep. In some example, the microcontroller 120 may be limited in the types of commands that it is able to receive during sleep. In some examples, the microcontroller 120 may require a reset in order to exit the sleep state. Various embodiments described herein relate to systems and techniques for causing the microcontroller 120 to reset, thereby allowing the microcontroller 120 to exit the sleep state and enter an enabled state. In the enabled state, the microcontroller 120 can resume full functionality.

In some embodiments, the microcontroller 120 may be configured to disable resets for a particular length of time. For example, the microcontroller 120 may be configured to disable resets (e.g., additional/subsequent resets) after the microcontroller 120 has been reset a first time to exit the sleep state. Such functionality may be incorporated into the microcontroller 120 by implementing a time delay that prevents reset of the microcontroller 120 after entering the enabled state. In some implementations, an integrated circuit (e.g., a second microcontroller) in communication with the microcontroller 120 may provide such delay functionality.

In some embodiments, the microcontroller 120 is instructed to enter the sleep state after manufacture of the injection device 102. Thereafter, the microcontroller 120 may remain in the sleep state until the injection device 102 is first used by the patient.

Still referring to FIG. 1, the patient may prime the injection device 102 (e.g., by performing a "prime shot") before using the injection device 102 for the first time. The prime shot may cause the microcontroller 120 to reset, thereby allowing the microcontroller 120 to exit the sleep state and resume full functionality. As described above, the prime shot is performed to remove air from the cartridge 104 and the needle 109. The patient may select a small dosage (e.g., two units of medicament) using the dosage knob 112 and press the injection button 111 while holding the injection device 102 with the needle 109 oriented upwards. The prime shot causes the piston 108 to drive the plunger 107 toward the member 115, thereby causing the plunger 107 and the member 115 to make physical contact with each other.

A top surface of the member 115 includes at least two conductive surfaces 122 that are electrically connected to the microcontroller 120. In particular, the conductive surfaces 122 may be connected to pins of the microcontroller 120 that are related to reset operations of the microcontroller 120 (e.g., pins that are connected to a reset circuit). When the member 115 and the plunger 107 made physical contact due to the prime shot, the conductive surfaces 122 make contact with a conductive element 124 that is incorporated in the drive mechanism 106, in particular, disposed on a bottom surface of the plunger 107. Before the prime shot is performed, the plunger 107 and the conductive element 124 may be spaced from the conductive surfaces 122 by a relatively short distance (e.g., less than 1 mm). The electrical contact may cause the pins of the microcontroller 120 to be electrically connected, thereby activating a reset circuit (e.g., triggering a reset switch) in the microcontroller 120 that initiates reset of the microcontroller 120. After reset, the microcontroller 120 may enter the enabled state in which the microcontroller 120 can resume full functionality for subsequent use by the patient.

While the injection device 102 illustrated in FIG. 1 has been described as including a member 115 that is disposed in the cartridge 104 and that includes conductive surfaces 122 configured to make contact with the conductive element 124 for resetting the microcontroller 120, any of various other types of members that include various types of conductive surfaces can alternatively or additionally be used. Examples of other types of members that can be used include ring-shaped members, disk-shaped members, pin-shaped members, etc. In some embodiments, the conductive surfaces may be ring-shaped, disk-shaped, and/or may be pins that extend toward the conductive element. Similarly, any of various other types of conductive elements can alternatively or additionally be used for making contact with the conductive surfaces of the member. Examples of other types of conductive elements that can be used include disk-shaped conductive elements that have a diameter substantially similar to the diameter of the cartridge 104 and/or the plunger 107, rod-shaped conductive elements that span the diameter of the plunger 107, ring-shaped conductive elements, conductive elements made of a conductive mesh material, etc.

In some embodiments, one or more additional techniques may be employed to cause the microcontroller 120 to reset and enter the sleep state. Such techniques may be alternative to or in addition to the technique described with respect to FIG. 1.

Figure 2:
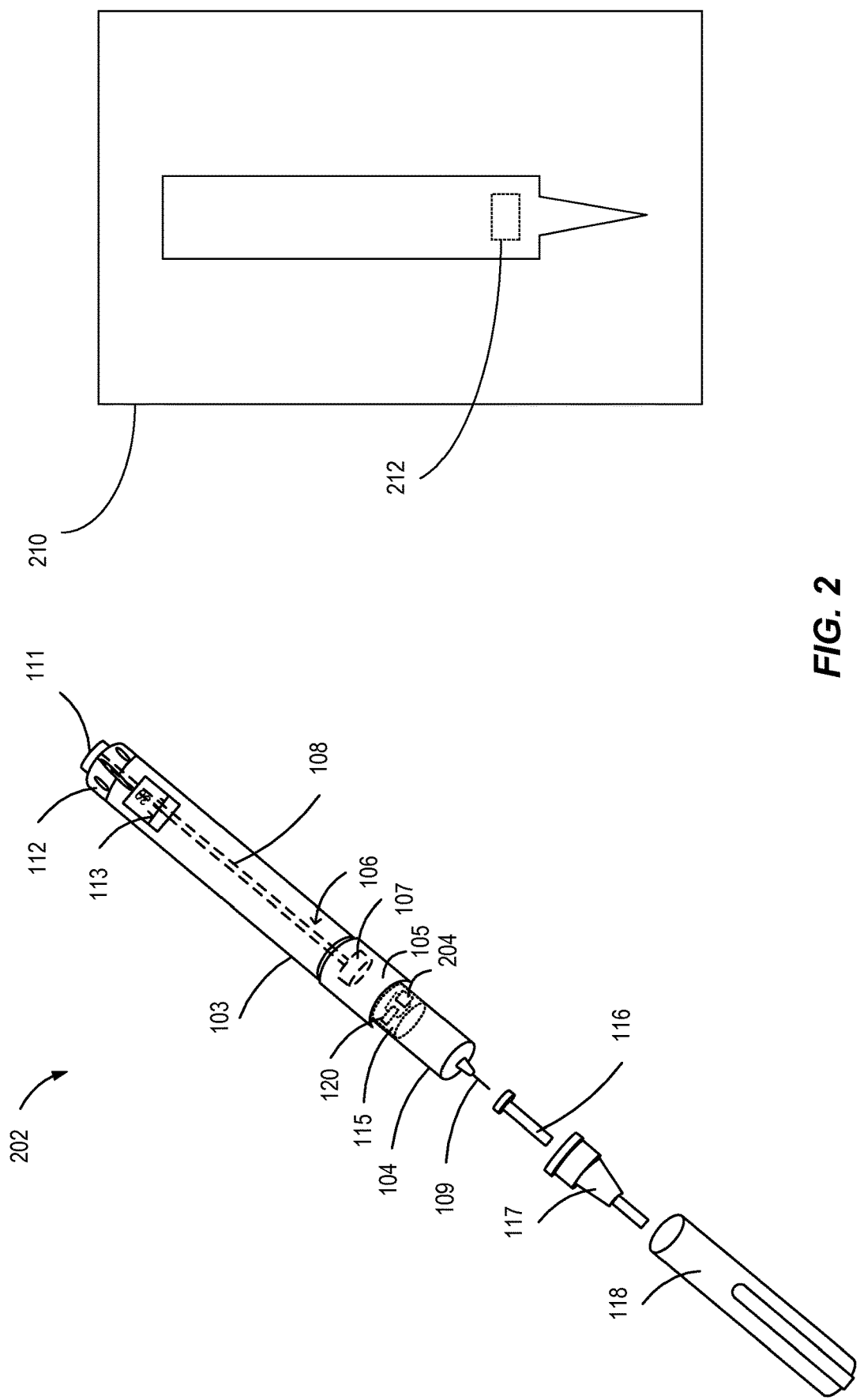

In some embodiments, the microcontroller 120 may be configured to receive a stimulus from one or more sensors that cause the microcontroller 120 to reset and enter the enabled state from the sleep state. FIG. 2 shows another example of an injection device 202. The injection device 202 is substantially similar to the injection device 102 of FIG. 1, with the differences noted herein. In particular, one or more of the components incorporated into the member 115 are different from those described with respect to FIG. 1.

The injection device 202 includes a magnetoresistance sensor 204 (e.g., a giant magnetoresistance sensor (GMR sensor)) that is electrically connected to the microcontroller 120. In particular, the magnetoresistance sensor 204 may be connected to pins of the microcontroller 120 that are related to reset operations (e.g., pins that are connected to the reset circuit). The magnetoresistance sensor 204 is configured to provide an electrical signal based on a sensed external magnetic field. For example, in the presence of a magnetic field that satisfies a threshold magnitude, the magnetoresistance sensor 204 is configured to provide no signal to the microcontroller 120, thereby allowing the microcontroller 120 to remain in the sleep state. When the magnetoresistance sensor 204 is no longer in the presence of the magnetic field that satisfies the threshold magnitude, the magnetoresistance sensor 204 is configured to provide a signal to the microcontroller 120 that causes the microcontroller 120 to reset and enter the enabled state. That is, when the magnetoresistance sensor 204 ceases to sense the magnetic field that satisfies the threshold magnitude, the magnetoresistance sensor 204 may provide a signal to the microcontroller 120 that causes particular pins of the microcontroller 120 to be electrically connected, thereby activating the reset circuit in the microcontroller 120 that initiates the reset and allows the microcontroller 120 to enter the enabled state in which the microcontroller 120 can resume full functionality for subsequent use by the patient.

In some embodiments, the injection device 202 may be packaged in packaging 210 after manufacture. The packaging 210 may include a cut-out having a shape substantially similar to the injection device 202 that allows the injection device 202 to fit in a predetermined orientation within the packaging 210. The packaging 210 may also include a magnet 212 (e.g., a permanent magnet) that is disposed at or near a position where the magnetoresistance sensor 204 resides when the injection device 202 is positioned in the packaging 210. In some embodiments, the magnet 212 may be embedded below a surface of the packaging (e.g., embedded in foam of cardboard of the packaging).

The magnet 212 is configured to provide a magnetic field to the magnetoresistance sensor 204 that has a magnitude that satisfies the threshold magnitude when the injection device 202 is positioned in the packaging 210. Therefore, after manufacture, the injection device 202 may be placed in the sleep state and inserted into the packaging 210. While the injection device 202 remains in the packaging 210, the magnet 212 provides a magnetic field of a magnitude that satisfies the threshold and prevents the magnetoresistance sensor 204 from providing a reset signal to the microcontroller 120.

Prior to first use by the patient, the patient may remove the injection device 202 from the packaging 210. When the injection device 202 is removed from proximity of the magnet 212, the magnetic field sensed by the magnetoresistance sensor 204 no longer satisfies the threshold magnitude, and in response, the magnetoresistance sensor 204 provides a signal to the microcontroller 120 that causes the microcontroller 120 to reset and enter the enabled state.

In some embodiments, the magnet 212 may be incorporated into one or more of the inner needle cap 116, the outer needle cap 117, and/or the cap 118 of the injection device. In such a configuration, the magnet 212 is configured to provide a magnetic field to the magnetoresistance sensor 204 that has a magnitude that satisfies the threshold magnitude when the cap 116, 117, and/or 118 is attached to the injection device 202. Prior to first use by the patient, the patient may remove the cap 116, 117, and/or 118 from the injection device 202, thereby causing the magnetic field sensed by the magnetoresistance sensor 204 to no longer satisfy the threshold magnitude, and in response, causing the microcontroller 120 to reset and enter the enabled state.

Figure 3:
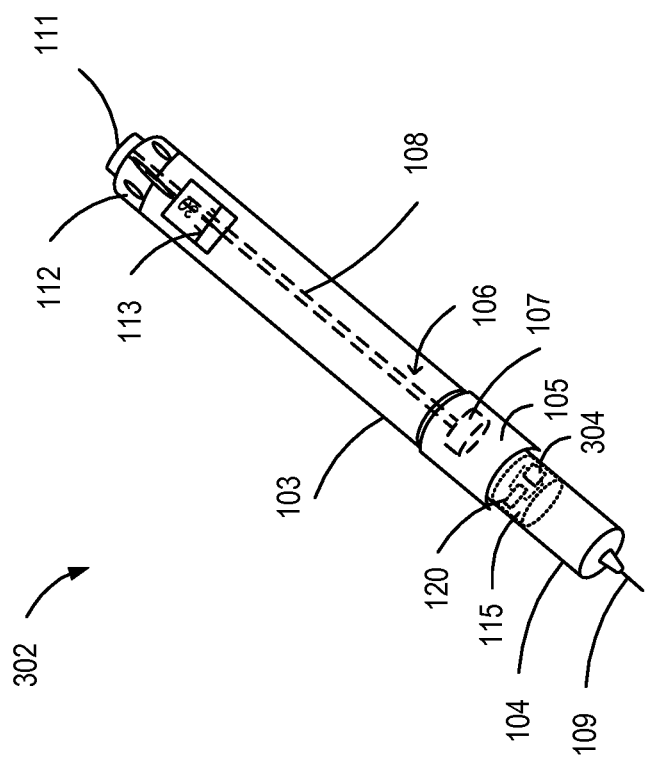

FIG. 3 shows another example of an injection device 302. Like the injection device 202 of FIG. 2, the injection device 302 is substantially similar to the injection device 102 of FIG. 1, except one or more of the components incorporated into the member 115 are different from those described with respect to FIG. 1.

The injection device 302 includes an optical sensor 304 that is electrically connected to the microcontroller 120. In some embodiments, the optical sensor 304 may be a photodiode (e.g., a reverse driven light-emitting diode (LED)) and/or a photoresistor. The optical sensor 304 may be connected to pins of the microcontroller 120 that are related to reset operations (e.g., pins that are connected to the reset circuit). The optical sensor 304 is configured to provide an electrical signal based on an intensity of sensed light. For example, if light is detected that satisfies a threshold intensity, the optical sensor 304 is configured to provide a signal to the microcontroller 120 that causes the microcontroller 120 to reset and enter the enabled state. In particular, the optical sensor 304 may provide a signal to the microcontroller 120 that causes particular pins of the microcontroller 120 to be electrically connected, thereby activating the reset circuit in the microcontroller 120 that initiates the reset and allows the microcontroller 120 to enter the enabled state in which the microcontroller 120 can resume full functionality for subsequent use by the patient.

In some embodiments, as described above, the microcontroller 120 may be configured to disable additional resets for a particular length of time after the microcontroller 120 resets, exits the sleep state, and enter the enabled state. Such functionality may prevent the microcontroller 120 from continuously remaining in a reset state (e.g., if ambient sensed light satisfies the threshold intensity).

In some embodiments, the cartridge 104 and the member 115 are made from a transparent material that allows light to pass therethrough, thereby allowing the optical sensor 304 to detect the light. In some embodiments, the cartridge 104 and the member 115 may include a transparent window positioned proximate to the optical sensor 304.

In some embodiments, the injection device 302 may be packaged in packaging after manufacture that limits and/or eliminates light from being provided to the optical sensor 304. In some embodiments, one or more stickers and/or covers may be applied to an outer surface of the cartridge 104 that limits and/or eliminates light from being provided to the optical sensor 304. In this way, the microcontroller 120 may remain in the sleep state while it resides in the packaging and/or while the stickers and/or covers are present. In some embodiments, the threshold intensity of light required to cause the optical sensor 304 to provide a reset signal to the microcontroller 120 may be such that ambient light does not trigger the reset. For example, prior to first use by the patient, the patient may remove the injection device 302 from the packaging and/or remove the sticker and/or cover, which alone does not trigger the reset of the microcontroller 120. The patient may be directed to hold the injection device 302 under a light source (e.g., a lamp) such that a sufficient intensity of light is provided to the optical sensor 304. In some embodiments, the patient may be directed to apply a laser light (e.g., from a laser pointer) to the optical sensor 304 to achieve the threshold intensity of light. Upon sensing light having an intensity that satisfies the threshold, the optical sensor 302 provides a signal to the microcontroller 120 that causes the microcontroller 120 to reset and enter the enabled state.

In some embodiments, instead or in addition to the injection device 302 including the optical sensor 304 that is configured to sense light, the injection device 302 may include an X-Ray diode that is configured to cause the microcontroller 120 to enter the enabled state when the X-Ray diode senses X-Ray radiation. The configuration of the X-Ray diode with respect to the microcontroller 120 may be substantially similar to that described above with respect to the optical sensor 304, except the X-Ray diode is configured to provide a reset signal when X-Ray radiation (rather than light that satisfies a threshold intensity) is sensed. In some embodiments, a user may be directed to use an X-Ray device to apply an X-Ray pulse to the X-Ray diode. In some embodiments, the X-Ray pulse may be applied by a medical professional (e.g., prior to receipt of the injection device 302 by the patient). For example, the X-Ray pulse used to reset the microcontroller 120 may be applied after manufacturing but prior to use by the patient in order to test the injection device 302, etc. In one or more of the embodiments described herein, one or more resets of the injection device may occur at different stages of test and/or use (e.g., after manufacture, during testing/calibration, before initial use by the patient, during an initial use by the patient, in subsequent uses by the patient, etc.).

Figure 4:
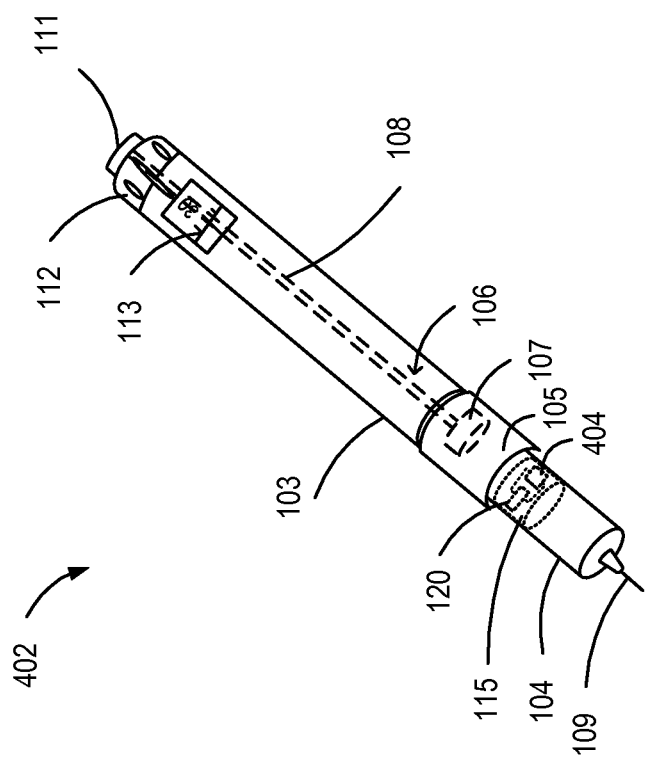

FIG. 4 shows another example of an injection device 402. Like the injection devices 202, 302 of FIGS. 2 and 3, the injection device 402 is substantially similar to the injection device 102 of FIG. 1, except one or more of the components incorporated into the member 115 are different from those described with respect to FIG. 1.

The injection device 402 includes a temperature-dependent resistor, such as a thermistor 404, that is electrically connected to the microcontroller 120. The thermistor 404 may be connected to pins of the microcontroller 120 that are related to reset operations (e.g., pins that are connected to the reset circuit). The thermistor 404 is configured to provide an electrical signal based on a sensed temperature. For example, if the thermistor 404 senses a temperature that satisfies a threshold, the thermistor 404 is configured to provide a signal to the microcontroller 120 that causes the microcontroller 120 to reset and enter the enabled state. In particular, the thermistor 404 may provide a signal to the microcontroller 120 that causes particular pins of the microcontroller 120 to be electrically connected, thereby activating the reset circuit in the microcontroller 120 that initiates the reset and allows the microcontroller 120 to enter the enabled state in which the microcontroller 120 can resume full functionality for subsequent use by the patient.

In some embodiments, following manufacture of the injection device 402, during shipping, and until receipt by the patient, the injection device 402 may be maintained within a particular temperature range. In some embodiments, the particular temperature range may be approximately 2° C. to about 8° C. In some embodiments, the particular temperature range may be approximately −4° C. to about 4° C. An appropriate temperature range may be chosen based on the particular medicament to ensure appropriate conditions. The temperature range in which the injection device 402 is maintained during shipping may be such that the threshold temperature is not satisfied, and as such, the thermistor 404 does not provide a reset signal to the microcontroller 120. Once the patient receives the injection device 402, the injection device may be subjected to a temperature (e.g., room temperature) that satisfies the threshold temperature. In turn, the thermistor 404 provides a signal to the microcontroller 120 that causes the microcontroller 120 to reset and enter the enabled state.

In some embodiments, the threshold temperature may be relatively large (e.g., greater than room temperature). For example, the threshold temperature may be such that achieving the threshold temperature may require application of heat to the thermistor 404 by the patient. In some examples, the patient may be directed to apply heat to the injection device 402, and in particular, to the portion of the injection device 404 that includes the thermistor 404. In some embodiments, the patient may be directed to use a heat gun and/or a laser to apply heat to the thermistor 404 to achieve the threshold temperature, thereby causing the thermistor 404 to provide a reset signal to the microcontroller 120.

Figure 5:
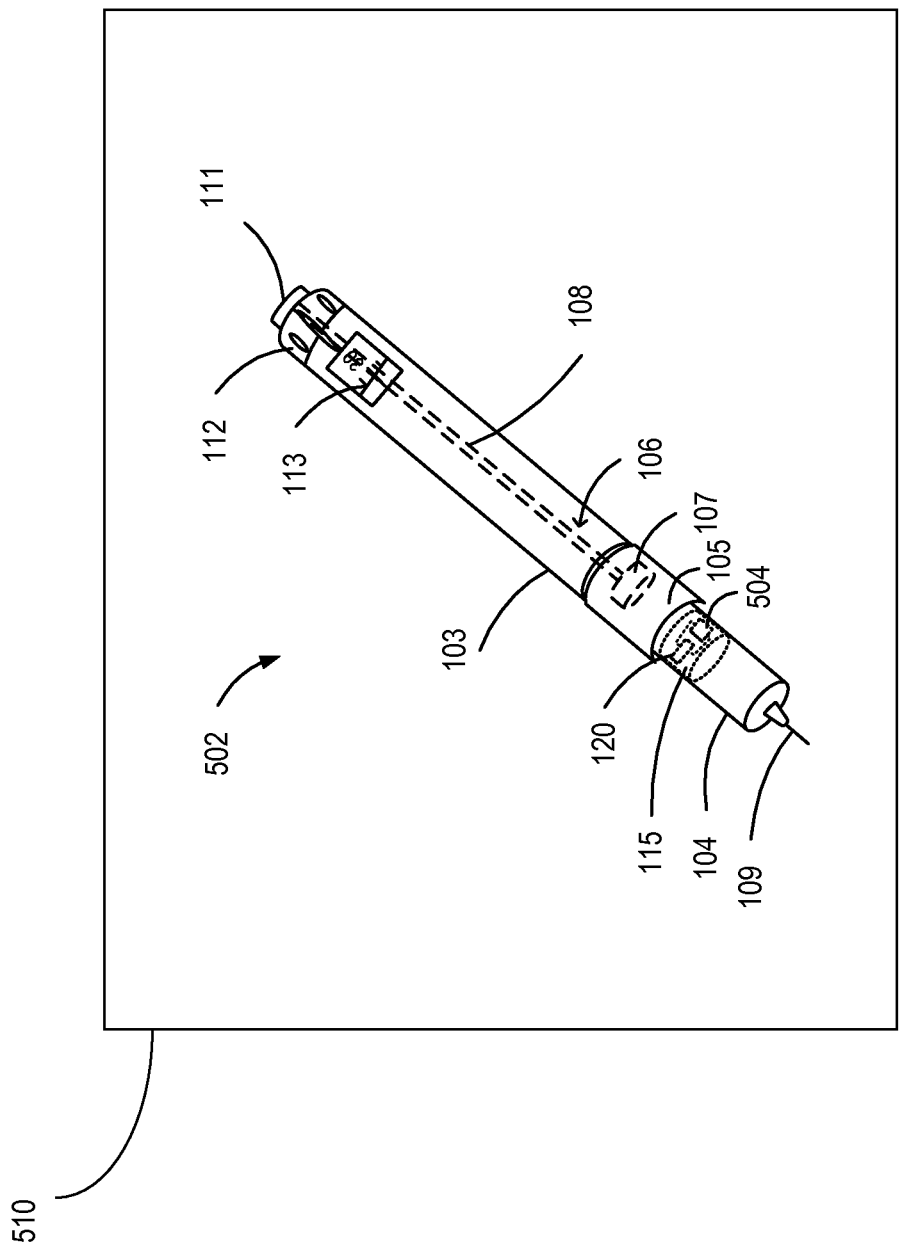

FIG. 5 shows another example of an injection device 502. Like the injection devices 202, 302, 402 of FIGS. 2-4, the injection device 502 is substantially similar to the injection device 102 of FIG. 1, except one or more of the components incorporated into the member 115 are different from those described with respect to FIG. 1.

The injection device 502 includes a Wi-Fi sensor 504 that is electrically connected to the microcontroller 120. In some embodiments, the Wi-Fi sensor 504 is a ceramic antenna. The Wi-Fi sensor 504 may be connected to pins of the microcontroller 120 that are related to reset operations (e.g., pins that are connected to the reset circuit). The Wi-Fi sensor 504 is configured to provide an electrical signal based on sensed Wi-Fi radiation. For example, if a Wi-Fi radiation is detected by the Wi-Fi sensor 504, the Wi-Fi sensor 504 is configured to provide a signal to the microcontroller 120 that causes the microcontroller 120 to reset and enter the enabled state. In particular, the Wi-Fi sensor 504 may provide a signal to the microcontroller 120 that causes particular pins of the microcontroller 120 to be electrically connected, thereby activating the reset circuit in the microcontroller 120 that initiates the reset and allows the microcontroller 120 to enter the enabled state in which the microcontroller 120 can resume full functionality for subsequent use by the patient.

In some embodiments, the Wi-Fi radiation detected by the Wi-Fi sensor 504 may originate from ambient Wi-Fi signals (e.g., from wireless routers, mobile electronic devices, etc.). Such Wi-Fi signals are typically prevalent in most households and business. In some embodiments, the injection device 502 may be provided as part of a system that includes the injection device 502 and packaging 510 that is configured to contain the injection device 502 and shield Wi-Fi radiation from the Wi-Fi sensor 504. The packaging 510 may include an electromagnetic protection layer. The injection device 502 may be packaged after manufacture and may remain in the packaging 510 during shipping and until receipt by the patient. Once the patient receives the injection device 502, the patient may remove the injection device 502 from the Wi-Fi shielding packaging 510, thereby exposing the Wi-Fi sensor 504 to ambient Wi-Fi radiation. Such Wi-Fi radiation causes the Wi-Fi sensor 504 to provide a reset signal to the microcontroller 120. In some embodiments, the packaging 510 is made from a material such as aluminum, although other suitable materials may also or alternatively be used.

In some embodiments, the Wi-Fi sensor 504 may provide the reset signal when the sensed Wi-Fi radiation satisfies a threshold magnitude (e.g., a threshold signal strength). In some embodiments, the patient may be directed to position the injection device 502 near a source of Wi-Fi signals (e.g., a wireless router, a mobile electronic device, etc.) in order to achieve the threshold magnitude.

Figure 6:
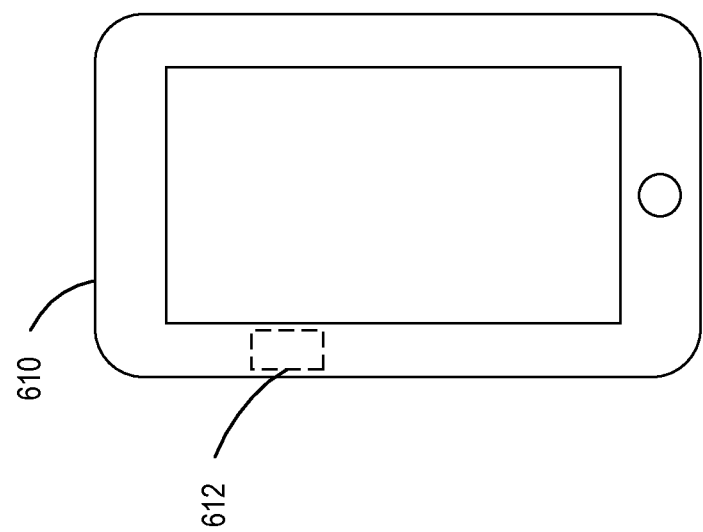
Figure 6:
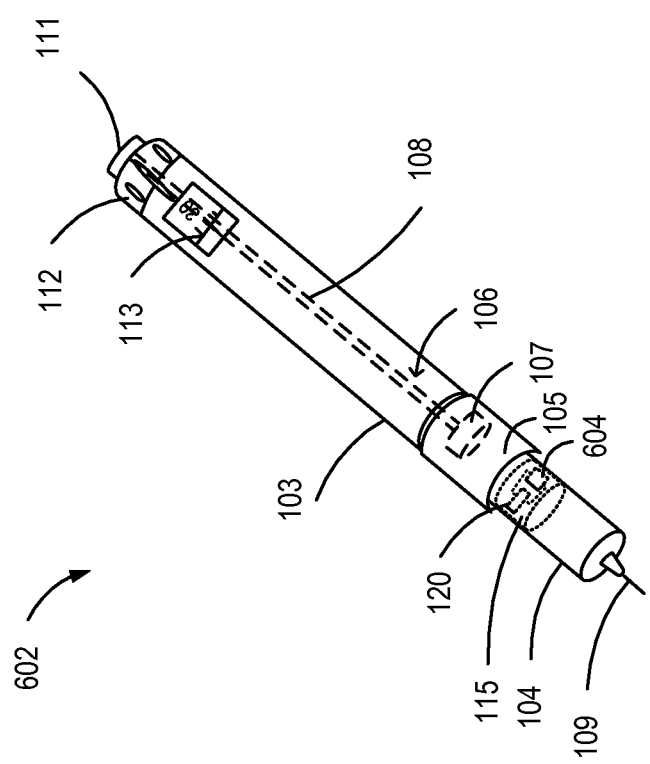

FIG. 6 shows another example of an injection device 602. Like the injection devices 202, 302, 402, 502 of FIGS. 2-5, the injection device 602 is substantially similar to the injection device 102 of FIG. 1, except one or more of the components incorporated into the member 115 are different from those described with respect to FIG. 1.

The injection device 602 includes an antenna and a sensor configured to receive electromagnetic signals (e.g., radio signals), such as a radio-frequency identification (RFID) sensor. In the example illustrated in FIG. 6, the injection device 602 includes a Near Field Communication (NFC) sensor 604 (e.g., an NFC reader and/or an NFC antenna) that is electrically connected to the microcontroller 120. The NFC sensor 604 may be connected to pins of the microcontroller 120 that are related to reset operations (e.g., pins that are connected to the reset circuit). The NFC sensor 604 is configured to receive an NFC signal from an NFC element 612 (e.g., an NFC tag, an NFC sensor/reader/antenna, etc.) of a computing device. In some embodiments, the computing device may be a mobile computing device such as a mobile phone 610 (e.g., a smartphone), although other computing device may also or alternatively be used, including but not limited to an electronic tablet, a laptop computer, a wearable electronic device, etc. Prior to first use by the patient, the patient may be directed to position the injection device 602 in proximity to the mobile phone 610. When the injection device 602 is within a sufficient distance of the mobile phone 610, the NFC sensor 604 receives the signal from the NFC element 612. In turn, the NFC sensor 604 is configured to provide a signal to the microcontroller 120 that causes the microcontroller 120 to reset and enter the enabled state. In particular, the NFC sensor 604 may provide a signal to the microcontroller 120 that causes particular pins of the microcontroller 120 to be electrically connected, thereby activating the reset circuit in the microcontroller 120 that initiates the reset and allows the microcontroller 120 to enter the enabled state in which the microcontroller 120 can resume full functionality for subsequent use by the patient.

In some embodiments, instead of or in addition to the injection device 602 including the NFC sensor 604, the injection device 602 may include one or more other sensors that are configured to communicate using a short-range wireless communication protocol. For example, the injection device 602 may include a sensor that includes a Bluetooth antenna that is configured to detect Bluetooth signals. Similarly, the mobile phone 610 may include a Bluetooth element (e.g., including a Bluetooth antenna) that is configured to provide Bluetooth signals to the Bluetooth antenna. Prior to first use by the patient, the patient may be directed to position the injection device 602 in proximity to the mobile phone 610. When the injection device 602 is within a sufficient distance of the mobile phone 610, the Bluetooth antenna receives the signal from the Bluetooth element, and in turn, the Bluetooth antenna provides a signal to the microcontroller 120 that causes the microcontroller 120 to reset and enter the enabled state.

Figure 7:
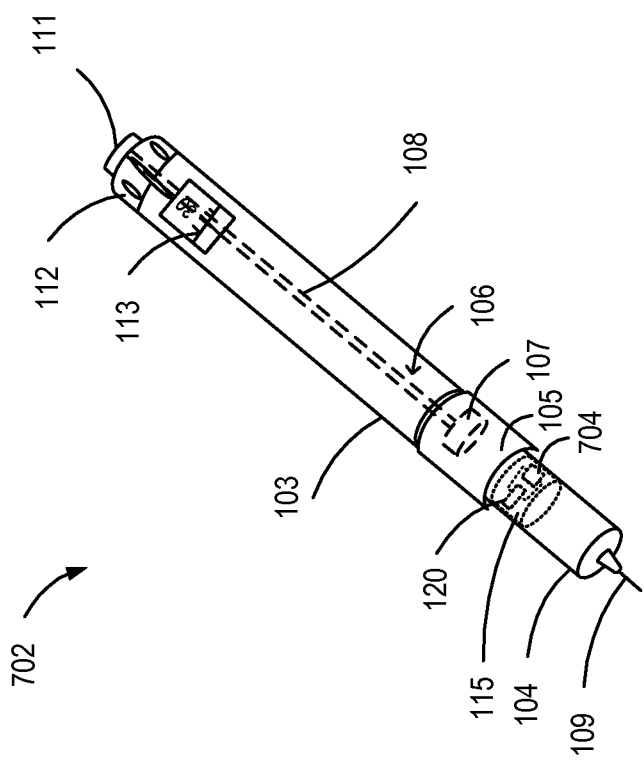

FIG. 7 shows another example of an injection device 702. Like the injection devices 202, 302, 402, 502, 602 of FIGS. 2-6, the injection device 702 is substantially similar to the injection device 102 of FIG. 1, except one or more of the components incorporated into the member 115 are different from those described with respect to FIG. 1.

The injection device 702 includes a resonant circuit 704 that is electrically connected to the microcontroller 120. The resonant circuit 704 may be connected to pins of the microcontroller 120 that are related to reset operations (e.g., pins that are connected to the reset circuit). The resonant circuit 704 may include an inductor, a capacitor, and a rectifier diode that are arranged with particular values such that the resonant circuit 704 is tuned to a particular frequency (e.g., a resonant frequency). The resonant circuit 704 is configured to sense a magnetic field having the particular frequency. When the resonant circuit 704 senses a magnetic field having the particular frequency, a voltage is generated in the resonant circuit 704 that causes the resonant circuit 704 to provide a signal to the microcontroller 120 that causes the microcontroller 120 to reset and enter the enabled state. In particular, the resonant circuit 704 may provide a signal to the microcontroller 120 that causes particular pins of the microcontroller 120 to be electrically connected, thereby activating the reset circuit in the microcontroller 120 that initiates the reset and allows the microcontroller 120 to enter the enabled state in which the microcontroller 120 can resume full functionality for subsequent use by the patient. In some embodiments, the resonant frequency may be in the range of approximately 50 kHz to 2 MHz (e.g., 100 kHz, 1 MHz, etc.). In some embodiments, the resonant frequency may be a frequency that is not typically generated by generally-available devices. In this way, unintended resetting of the microcontroller can be minimized.

In some embodiments, the magnetic field having the particular (e.g., resonant) frequency may be provided by a separate electronic device. Such an electronic device may be provided along with the injection device 702 to the patient. In some embodiments, such an electronic device that is capable of generating a magnetic field of a particular frequency may improve security. In particular, because a magnetic field having a particular frequency is required to reset the microcontroller 120, only those who have access to a device capable of generating such a magnetic field are able to reset the microcontroller 120 and cause the microcontroller 120 to enter the enabled state.

Figure 8A:
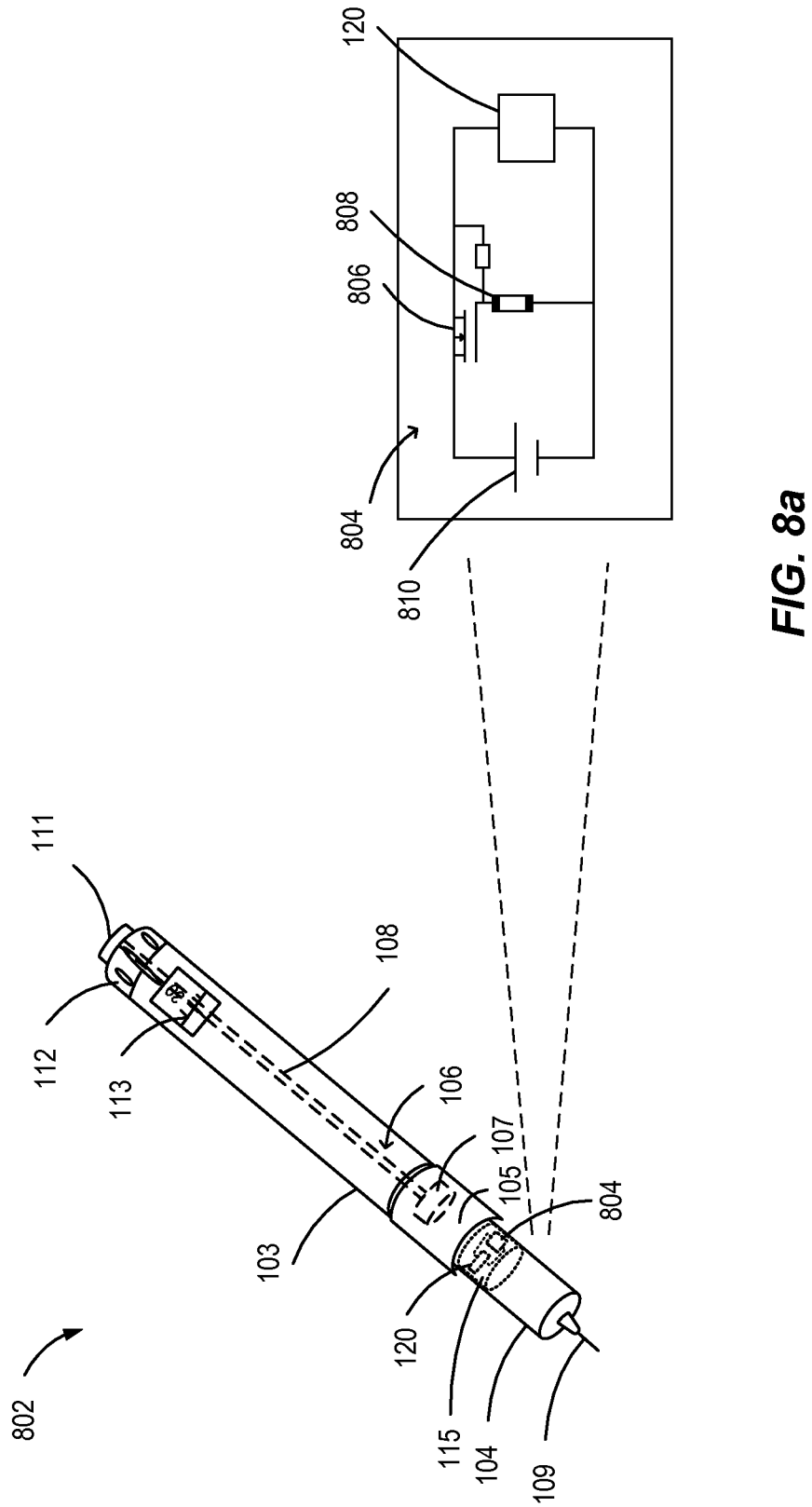
Figure 8B:
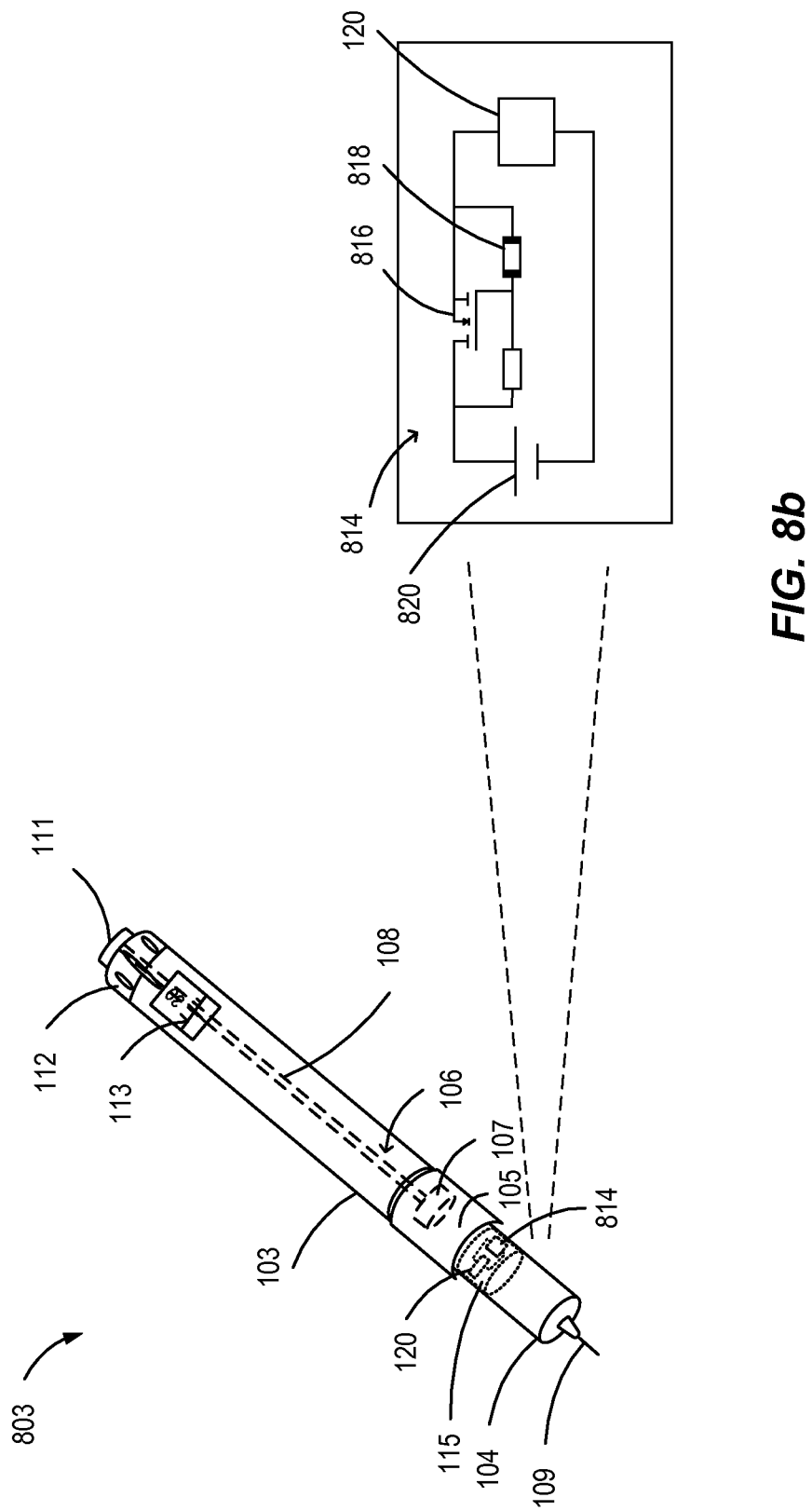

FIGS. 8a and 8b show other examples of injection devices 802, 803. Like the injection devices 202, 302, 402, 502, 602, 702 of FIGS. 2-7, the injection devices 802, 803 are substantially similar to the injection device 102 of FIG. 1, except one or more of the components incorporated into the member 115 are different from those described with respect to FIG. 1.

Referring to FIG. 8a, the injection device 802 includes a circuit 804 that is electrically connected to the microcontroller 120. The circuit 804 may be connected to pins of the microcontroller 120 that are related to reset operations (e.g., pins that are connected to the reset circuit). The circuit 804 may include a transistor 806, a fuse 808, and a power source such as a battery 810. In the illustrated example, the circuit 804 is arranged such that the transistor 806 is a self-conducting N-MOS field-effect transistor (FET), (e.g., a normally open N-MOS FET), although other transistors, such as a P-MOS FET, may additionally or alternatively be used. In an initial state of the circuit 804 (e.g., when the fuse 808 is not blown), a reset signal is not provided to the microcontroller 120. When the fuse 808 is blown, the transistor 806 switches in such a way that a reset signal (e.g., in the form of an input voltage or current) is applied to the microcontroller 120, thereby causing the microcontroller 120 to reset, exit the sleep state, and enter the enabled state. In particular, upon the fuse 808 being blown, the transistor 806 may provide a signal to the microcontroller 120 that causes particular pins of the microcontroller 120 to be electrically connected, thereby activating the reset circuit in the microcontroller 120 that initiates the reset and allows the microcontroller 120 to enter the enabled state in which the microcontroller 120 can resume full functionality for subsequent use by the patient.

In some embodiments, the circuit 804 may be arranged such that in the initial state (e.g., when the fuse 808 is not blown), the transistor 806 electrically isolates the microcontroller 120 from the battery 810. When the fuse 808 is blown, the transistor 806 switches in such a way that the transistor 806 electrically connects the microcontroller 120 to the battery 810. In this way, the microcontroller 120 may remain powered off (e.g., as opposed to remaining in the sleep state) until ready for use by the patient. Upon being connected to the battery 810, the microcontroller 120 may enter the enabled state in which the microcontroller 120 can resume full functionality for subsequent use by the patient.

Referring to FIG. 8b, the injection device 803 includes a circuit 814 that is electrically connected to the microcontroller 120. The circuit 814 may be connected to pins of the microcontroller 120 that are related to reset operations (e.g., pins that are connected to the reset circuit). The circuit 814 may include a transistor 816, a fuse 818, and a power source such as a battery 820. The circuit 814 may operate in a manner substantially similar to the circuit 804 described above with respect to FIG. 8a, except in the illustrated example, the circuit 814 is arranged such that the transistor 816 is a self-locking N-MOS field-effect transistor (FET), (e.g., a normally closed N-MOS FET), although other transistors, such as a P-MOS FET, may additionally or alternatively be used. In an initial state of the circuit 814 (e.g., when the fuse 818 is not blown), a reset signal is not provided to the microcontroller 120. When the fuse 818 is blown, the transistor 816 switches in such a way that a reset signal (e.g., in the form of an input voltage or current) is applied to the microcontroller 120, thereby causing the microcontroller 120 to reset, exit the sleep state, and enter the enabled state. In particular, upon the fuse 818 being blown, the transistor 816 may provide a signal to the microcontroller 120 that causes particular pins of the microcontroller 120 to be electrically connected, thereby activating the reset circuit in the microcontroller 120 that initiates the reset and allows the microcontroller 120 to enter the enabled state in which the microcontroller 120 can resume full functionality for subsequent use by the patient.

Like the circuit 804 of FIG. 8a, in some embodiments, the circuit 814 may be arranged such that in the initial state (e.g., when the fuse 818 is not blown), the transistor 816 electrically isolates the microcontroller 120 from the battery 820. When the fuse 818 is blown, the transistor 816 switches in such a way that the transistor 816 electrically connects the microcontroller 120 to the battery 820. In this way, the microcontroller 120 may remain powered off (e.g., as opposed to remaining in the sleep state) until ready for use by the patient. Upon being connected to the battery 820, the microcontroller 120 may enter the enabled state in which the microcontroller 120 can resume full functionality for subsequent use by the patient.

The circuit 804, 814 may have configurations different from those illustrated in FIGS. 8a and 8b. For example, in some embodiments, the circuits 804, 814 may include one or more additional transistors 806, 816 and/or one or more additional fuses 808, 818.

The fuses 806, 816 may be blown in response to application of a light source (e.g., a laser light source). For example, the laser light may provide heat to the fuse 806, 816 that causes the fuse 806, 816 to blow. The laser light may be supplied by a separate electronic device that is provided along with the injection device 802, 803. The patient may be directed to operate the electronic device to apply the laser light in order to blow the fuse 806, 816 before initial use of the injection device 802, 803 by the patient. In some embodiments, the cartridge 104 and the member 115 are made from a transparent material that allows light to pass therethrough, thereby allowing the laser light to be applied to the fuse 806, 816. In some embodiments, the cartridge 104 and the member 115 may include a transparent window positioned proximate to the fuse 806, 816.

Figure 9:
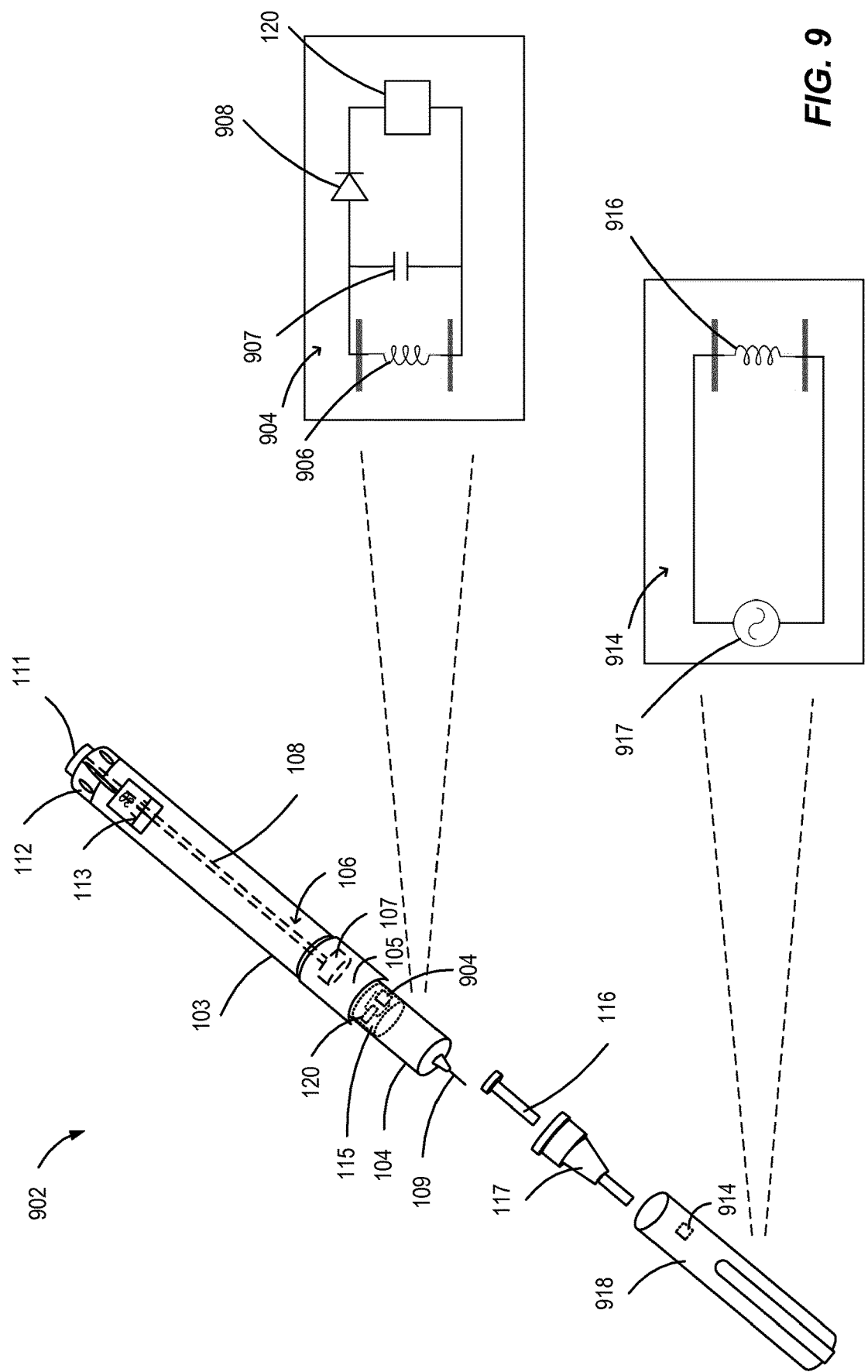

FIG. 9 shows another example of an injection device 902. Like the injection devices 202, 302, 402, 502, 602, 702, 802, 803 of FIGS. 2-8b, the injection device 902 is substantially similar to the injection device 102 of FIG. 1, except one or more of the components incorporated into the member 115 are different from those described with respect to FIG. 1. Further, additional components are incorporated into a cover 918.

In the illustrated example, the injection device 902 is configured to harvest energy from a power source, and the harvested energy is used to power the microcontroller 120. In particular, the injection device 902 includes a second circuit 904 that is configured receive power from a first circuit 914 incorporated into the cover 918 (e.g., the needle cover).

The first circuit 914 includes a power source 917 (e.g., an AC power source) and a first inductive coil 916 (e.g., a primary coil). The power source 917 may be supplied by an AC power outlet, and the cover 918 may include a power cord that is configured to plug into the AC power outlet to supply AC power to the circuit 914. In some embodiments, the cover 918 may be incorporated into a mount (e.g., a stand) that is configured to support the injection device 902 when not in use. The power source 917 provides power to the first inductive coil 916 to cause the first inductive coil 916 to generate an electromagnetic field to be received by the second circuit 904.

The second circuit 904 generates power from the electromagnetic field generated by the first inductive coil 916. In particular, the second circuit 904 includes a second inductive coil 906 that is configured to receive the electromagnetic field from the first inductive coil 916 and use the received electromagnetic field to generate power. The second circuit 904 also includes a capacitor, such as a supercapacitor 907, that is configured to store the power generated by the second inductive coil 906. The second circuit 904 also includes a diode 908 that allows DC to pass therethrough. The supercapacitor 907 can provide stored power to the microcontroller 120 via the diode 908. In some embodiments, the supercapacitor 907 is provided in place of a separate power source (e.g., in place of a battery). In this way, the injection device 902 can operate without need of a battery (e.g., a rechargeable battery). However, in some embodiments, the supercapacitor 907 may be replaced with another power source (e.g., rechargeable power source), such as a rechargeable battery.

When the cap 918 is within a threshold range of the member 115 (e.g., when the cap 918 is attached to the housing 103 of the injection device 902), the first inductive coil 916 and the second inductive coil 906 form an electromagnetic link that allows for inductive charging. In this way, the first inductive coil 916 and the second inductive coil 906 act as a transformer that charges the supercapacitor 907. When the cap 918 is no longer within the threshold range of the member 115 (e.g., when the cap 918 is removed from the housing 103 prior to use by the patient), the electromagnetic link is temporarily broken and inductive charging ceases. However, even when the link is broken, the power stored in the supercapacitor 907 can be used to power the microcontroller 120. Once the power stored by the supercapacitor 907 is depleted, the cap 918 can be reattached to the housing 103 and the supercapacitor 907 can be recharged by inductive charging.

In some embodiments, the supercapacitor 907 is an electric double-layer capacitor (EDLC) which provides relatively high-capacity power storage (e.g., compared to conventional capacitors). The supercapacitor 907 may have a capacitance value significantly higher than conventional capacitors and may store 10 to 100 times more energy per unit volume or mass than electrolytic capacitors. Further, the supercapacitor 907 may accept and deliver charge at a significantly higher rate than that typically provided by a rechargeable battery.

Figure 10:
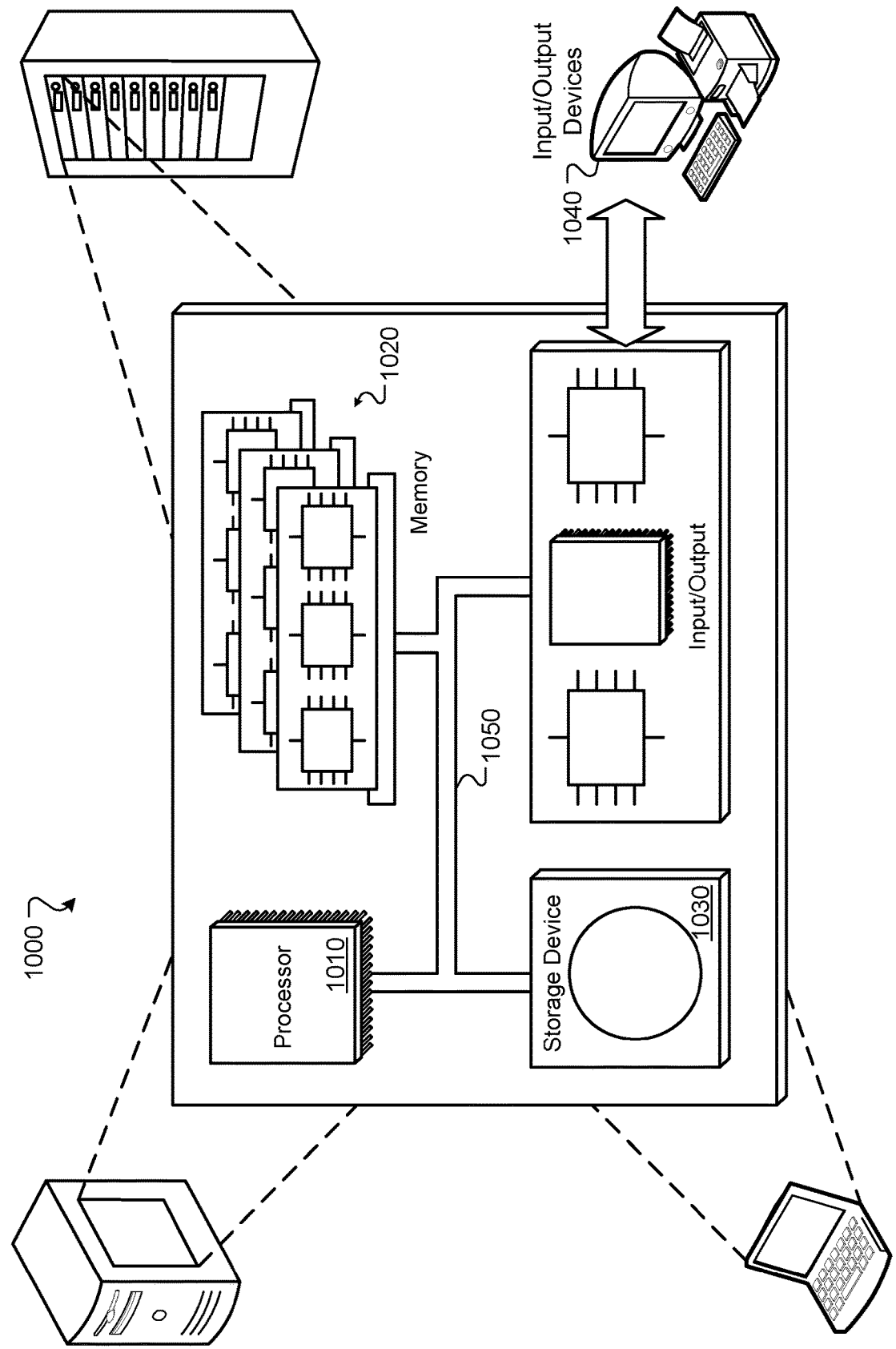
FIG. 10 is a block diagram of an example computer system.

FIG. 10 is a block diagram of an example computer system 100. For example, the microcontroller 120 of FIGS. 1-9 and/or the computing device (e.g., the mobile phone 610) of FIG. 6 may be an example of the computer system 1000. In some implementations, the injection device may be configured to interact with a separate computer system 1000. The system 1000 includes a processor 1010, a memory 1020, a storage device 1030, and an input/output device 1040. Each of the components 1010, 1020, 1030, and 1040 can be interconnected, for example, using a system bus 1050. The processor 1010 is capable of processing instructions for execution within the system 1000. The processor 1010 can be a single-threaded processor, a multi-threaded processor, or a quantum computer. The processor 1010 is capable of processing instructions stored in the memory 1020 or on the storage device 1030. The processor 1010 may execute operations such as causing the injection device to carry out one or more of the operations described above.

The memory 1020 stores information within the system 1000. In some embodiments, the memory 1020 is a computer-readable medium. The memory 1020 can, for example, be a volatile memory unit or a non-volatile memory unit. In some embodiments, the memory 1020 stores information related to the operations described above.

The storage device 1030 is capable of providing mass storage for the system 1000. In some embodiments, the storage device 1030 is a non-transitory computer-readable medium. The storage device 1030 can include, for example, a hard disk device, an optical disk device, a solid-state drive, a flash drive, magnetic tape, or some other large capacity storage device. The storage device 1030 may alternatively be a cloud storage device, e.g., a logical storage device including multiple physical storage devices distributed on a network and accessed using a network. In some embodiments, the information stored on the memory 1020 can also or instead be stored on the storage device 1030.

The input/output device 1040 provides input/output operations for the system 1000. In some embodiments, the input/output device 1040 includes one or more of network interface devices (e.g., an Ethernet card), a serial communication device (e.g., an RS-232 port), and/or a wireless interface device (e.g., a short-range wireless communication device, an 802.11 card, a 3G wireless modem, or a 4G wireless modem). In some embodiments, the input/output device 1040 includes driver devices configured to receive input data and send output data to other input/output devices, e.g., a keyboard, a printer, and display devices (e.g., such as the dosage window 113). In some embodiments, mobile computing devices, mobile communication devices, and other devices are used.

In some embodiments, the system 1000 is a microcontroller. A microcontroller is a device that contains multiple elements of a computer system in a single electronics package. For example, the single electronics package could contain the processor 1010, the memory 1020, the storage device 1030, and input/output devices 1040.

Although an example processing system has been described in FIG. 10, embodiments of the subject matter and the functional operations described above can be embodiments in other types of digital electronic circuitry, or in computer software, firmware, or hardware, including the structures disclosed in this specification and their structural equivalents, or in combinations of one or more of them. Embodiments of the subject matter described in this specification can be implemented as one or more computer program products, e.g., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoylgamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (such as, for example, adjustments, additions, or removals) of various components of the substances, formulations, apparatuses, methods, systems, devices, and embodiments described herein may be made without departing from the full scope and spirit of the present inventive concepts, which encompass such modifications and any equivalents thereof.

A number of embodiments of the systems and techniques described herein have been presented. Nevertheless, it will be understood that various modifications may be made without departing from the spirit and scope of such system and techniques. Accordingly, other embodiments are within the scope of the following claims.

Clause 1: A drug injection device (102) comprising:
a cartridge (104) configured to hold a volume of a drug; one or more processors (120) configured to operate in at least an enabled state and a sleep state, wherein the one or more processors (120) are configured to control an operation of the drug injection device (102) while the one or more processors (120) are in the enabled state; a member (115) disposed in the cartridge (104), the member (115) including at least two conductive surfaces (122) electrically connected to the one or more processors (120); and a drive mechanism (106) including a conductive element (124) spaced from the at least two conductive surfaces (122), wherein the one or more processors (120) are configured to enter the enabled state from the sleep state when the conductive element (124) makes electrical contact with the at least two conductive surfaces (122).

Clause 2: The drug injection device (102) of clause 1, wherein the member (115) is a stopper, and the conductive element (124) is disposed on a bottom surface of a plunger (107) of the drive mechanism (106).

Clause 3: The drug injection device (102) of clause 1, wherein the conductive element (124) is configured to move toward the member (115) and make electrical contact with the at least two conductive surfaces (122) in response to engagement of the drive mechanism (106).

Clause 4: The drug injection device (102) of clause 3, wherein the drive mechanism (106) is engaged during priming of the drug injection device (102).

Clause 5: The drug injection device (102) of clause 1, wherein the conductive element (124) making electrical contact with the at least two conductive surfaces (122) causes a reset circuit in the one or more processors (120) to be activated.

Clause 6: The drug injection device (102) of clause 1, further comprising one or more non-transitory computer-readable medium (1030) storing instructions operable to cause the one or more processors (120) to control the operation of the drug injection device (102).

Clause 7: The drug injection device (102) of clause 6, wherein the one or more non-transitory computer-readable medium (1030) includes a ferroelectric random access memory (FRAM) that is configured to store data without a continuous supply of power.

Clause 8: A drug injection device (202, 302, 402, 502, 602, 702) comprising:
a cartridge (104) configured to hold a volume of a drug; one or more processors (120) configured to operate in at least an enabled state and a sleep state, wherein the one or more processors (120) are configured to control an operation of the drug injection device (202, 302, 402, 502, 602, 702) while the one or more processors (120) are in the enabled state; and a sensor in communication with the one or more processors (120), wherein the sensor is configured to cause the one or more processors (120) to enter the enabled state from the sleep state in response to a stimulus.

Clause 9: The drug injection device (202) of clause 8, wherein the sensor is a magnetoresistance sensor (204) that is configured to cause the one or more processors (120) to enter the enabled state when the magnetoresistance sensor (204) ceases to sense a magnetic field that satisfies a threshold magnitude.

Clause 10: The drug injection device (202) of clause 9, wherein the drug injection device (202) is configured to reside in packaging (210) that includes a magnet (212) that provides the magnetic field that satisfies the threshold magnitude, wherein the one or more processors (120) enter the enabled state when the drug injection device (202) is removed from the packaging (210).

Clause 11: The drug injection device (202) of clause 9, further comprising a cap (116, 117, 118) that is configured to attach to a housing (103) of the drug injection device (202), the cap (116, 117, 118) including a magnet (212) that provides the magnetic field that satisfies the threshold magnitude, wherein the one or more processors (120) enter the enabled state when the cap (116, 117, 118) is removed from the housing (103).

Clause 12: The drug injection device (302) of clause 8, wherein the sensor includes one or both of a photodiode or a photoresistor that is configured to cause the one or more processors (120) to enter the enabled state when the photodiode or photoresistor senses light that satisfies a threshold intensity.

Clause 13: The drug injection device (402) of clause 8, wherein the sensor is a thermistor (404) that is configured to cause the one or more processors (120) to enter the enabled state when the thermistor (404) senses a temperature that satisfies a threshold.

Clause 14: The drug injection device (302) of clause 8, wherein the sensor is an X-Ray diode that is configured to cause the one or more processors (120) to enter the enabled state when the X-Ray diode senses X-Ray radiation.

Clause 15: The drug injection device (502) of clause 8, wherein the sensor is a Wi-Fi sensor (504) that is configured to cause the one or more processors (120) to enter the enabled state when the Wi-Fi sensor (504) senses Wi-Fi radiation.

Clause 16: The drug injection device (502) of clause 15, wherein the drug injection device (502) is configured to reside in packaging (510) that shields Wi-Fi radiation, wherein the one or more processors (120) enter the enabled state when the drug injection device (502) is removed from the packaging (510).

Clause 17: The drug injection device (602) of clause 8, wherein the sensor is a Near Field Communication (NFC) sensor (604) that is configured to cause the one or more processors (120) to enter the enabled state when the NFC sensor (604) receives an NFC signal from a computing device.

Clause 18: The drug injection device (602) of clause 17, wherein the computing device is a mobile phone (610).

Clause 19: The drug injection device (602) of clause 8, wherein the sensor includes a Bluetooth antenna that is configured to cause the one or more processors (120) to enter the enabled state when the Bluetooth antenna receives a Bluetooth signal from a computing device.

Clause 20: The drug injection device (702) of clause 8, wherein the sensor includes a resonant circuit (704) that is configured to cause the one or more processors (120) to enter the enabled state when the resonant circuit (704) senses a magnetic field having a resonant frequency.

Clause 21: A system comprising:
a drug injection device (502) comprising:
a cartridge (104) configured to hold a volume of a drug; one or more processors (120) configured to operate in at least an enabled state and a sleep state, wherein the one or more processors (120) are configured to control an operation of the drug injection device (502) while the one or more processors (120) are in the enabled state; and a Wi-Fi sensor (504) in communication with the one or more processors (120), wherein the Wi-Fi sensor (504) is configured to cause the one or more processors (120) to enter the enabled state from the sleep state when the Wi-Fi sensor (504) senses Wi-Fi radiation; and packaging (510) configured to contain the drug injection device (502) after manufacture and until initial use by a patient, wherein the packaging (510) includes a material that shields Wi-Fi radiation to prevent the one or more processors (120) from entering the enabled state until the drug injection device (502) is removed from the packaging (510).

Clause 22: A drug injection device (802, 803) comprising: a cartridge (104) configured to hold a volume of a drug; one or more processors (120) configured to operate in at least an enabled state and a sleep state, wherein the one or more processors (120) are configured to control an operation of the drug injection device (802, 803) while the one or more processors (120) are in the enabled state; and a circuit (804, 814) electrically connected to the one or more processors (120), the circuit (804, 814) comprising one or more transistors (806, 816) and one or more fuses (808, 818), wherein the one or more transistors (806, 816) are configured to cause the one or more processors (120) to enter the enabled state from the sleep state in response to the one or more fuses (808, 818) being blown.

Clause 23: The drug injection device (802, 803) of clause 22, wherein the one or more fuses (806, 816) are blown in response to application of laser light.

Clause 24: The drug injection device (802, 803) of clause 23, wherein the laser light is applied by an electronic device provided with the drug injection device (802, 803).

Clause 25: The drug injection device (802, 803) of clause 23, wherein heat provided by the laser light causes the one or more fuses (806, 816) to blow.

Clause 26: A drug injection device (802, 803) comprising: a cartridge (104) configured to hold a volume of a drug; one or more processors (120) configured to control an operation of the drug injection device (802, 803); and a circuit (804, 814) electrically connected to the one or more processors (120), the circuit (804, 814) comprising a battery (810, 820), one or more transistors (806, 816), and one or more fuses (808, 818), wherein the one or more transistors (806, 816) electrically isolate the one or more processors (120) from the battery (810, 820) when the one or more fuses (808, 818) are in a non-blown state, and the one or more transistors (806, 816) electrically connect the one or more processors (120) to the battery (810, 820) when the one or more fuses (808, 818) are blown.

Clause 27: The drug injection device (802, 803) of clause 26, wherein the one or more fuses (808, 818) are blown in response to application of laser light.

Clause 28: The drug injection device (802, 803) of clause 27, wherein the laser light is applied by an electronic device provided with the drug injection device (802, 803).

Clause 29: The drug injection device (802, 803) of clause 27, wherein heat provided by the laser light causes the one or more fuses (808, 818) to blow.

Clause 30: A drug injection device (902) comprising: a cartridge (104) configured to hold a volume of a drug; one or more processors (120) configured to control an operation of the drug injection device (902); a cover (918) configured to attach to a housing (103) of the drug injection device (902), wherein the cover (918) includes a first inductive coil (916) configured to electrically connect to a power source (917); and a circuit (904) electrically connected to the one or more processors (120), the circuit (904) comprising a second inductive coil (906) and a supercapacitor (907), wherein the second inductive coil (906) is configured to receive an electromagnetic field from the first inductive coil (916) and generate power to be stored by the supercapacitor (907) and provided to the one or more processors (120).

The invention claimed is:

1. A drug injection device comprising:
   a cartridge configured to hold a volume of a drug;
   one or more processors configured to operate in at least an enabled state and a sleep state, wherein the one or more processors are configured to control an operation of the drug injection device while the one or more processors are in the enabled state;
   a member disposed in the cartridge, the member including at least two conductive surfaces electrically connected to the one or more processors; and
   a drive mechanism including a conductive element spaced from the at least two conductive surfaces, wherein the one or more processors are configured to enter the enabled state from the sleep state when the conductive element makes electrical contact with the at least two conductive surfaces,
   wherein the member is configured to be displaced by the drive mechanism when the drive mechanism makes physical contact with the member.

2. The drug injection device of claim 1, wherein the member is a stopper, and the conductive element is disposed on a bottom surface of a plunger of the drive mechanism.

3. The drug injection device of claim 1, wherein the conductive element is configured to move toward the member and make electrical contact with the at least two conductive surfaces in response to an engagement of the drive mechanism.

4. The drug injection device of claim 3, wherein the drive mechanism is configured to be engaged during priming of the drug injection device.

5. The drug injection device of claim 1, wherein the conductive element making electrical contact with the at least two conductive surfaces causes a reset circuit in the one or more processors to be activated.

6. The drug injection device of claim 1, further comprising one or more non-transitory computer-readable medium storing instructions operable to cause the one or more processors to control the operation of the drug injection device.

7. The drug injection device of claim 6, wherein the one or more non-transitory computer-readable medium includes a ferroelectric random access memory (FRAM) that is configured to store data without a continuous supply of power.

* * * * *